United States Patent [19]

Jayaraman

[11] Patent Number: 5,725,548
[45] Date of Patent: Mar. 10, 1998

[54] SELF-LOCKING STENT AND METHOD FOR ITS PRODUCTION

[75] Inventor: Swaminathan Jayaraman, Bangalore, India

[73] Assignee: Iowa India Investments Company Limited, Isle of Man

[21] Appl. No.: 629,318

[22] Filed: Apr. 8, 1996

[51] Int. Cl.⁶ .................................................. A61M 29/00
[52] U.S. Cl. .......................... 606/198; 606/192; 623/1; 623/12
[58] Field of Search ............................... 606/191, 192, 606/194, 195, 198; 623/1, 12

[56] References Cited

U.S. PATENT DOCUMENTS

| | | |
|---|---|---|
| 4,733,665 | 3/1988 | Palmaz . |
| 4,739,762 | 4/1988 | Palmaz . |
| 4,776,337 | 10/1988 | Palmaz . |
| 5,059,211 | 10/1991 | Stack et al. ............................... 606/198 |
| 5,102,417 | 4/1992 | Palmaz . |
| 5,195,984 | 3/1993 | Schatz . |
| 5,234,457 | 8/1993 | Andersen . |
| 5,306,286 | 4/1994 | Stack et al. ............................... 606/198 |
| 5,330,500 | 7/1994 | Song . |
| 5,344,425 | 9/1994 | Sawyer . |
| 5,344,426 | 9/1994 | Lau et al. . |
| 5,356,423 | 10/1994 | Tihon et al. ............................... 606/194 |
| 5,389,106 | 2/1995 | Tower . |
| 5,419,760 | 5/1995 | Narciso, Jr. ............................... 606/194 |
| 5,421,955 | 6/1995 | Lau et al. ............................... 606/198 |
| 5,423,885 | 6/1995 | Williams ............................... 606/194 |
| 5,441,515 | 8/1995 | Khosravi et al. ............................... 606/194 |
| 5,443,458 | 8/1995 | Eury ............................... 606/198 |
| 5,443,496 | 8/1995 | Schwartz et al. . |
| 5,443,498 | 8/1995 | Fontaine . |
| 5,443,500 | 8/1995 | Sigwart . |
| 5,449,373 | 9/1995 | Pinchasik et al. . |
| 5,449,382 | 9/1995 | Dayton ............................... 606/194 |

Primary Examiner—Michael Buiz
Assistant Examiner—Patrick W. Rasche
Attorney, Agent, or Firm—James E. Larson; Larson & Larson, P.A.

[57] ABSTRACT

A tubular member is formed from a flat sheet having opposed longitudinal edges. Rows of parallel longitudinal slots are cut in the flat sheet and at least three holes are cut along the opposed longitudinal edges. The holes are aligned with the holes on the opposed edge and sutured together to form the tubular member. The tubular member is compressed over a balloon catheter and thereafter permanently positioned within a desired portion of a blood vessel.

13 Claims, 2 Drawing Sheets

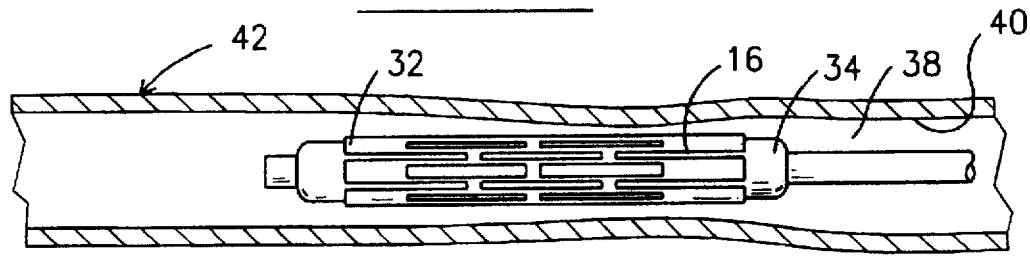
Fig. 4
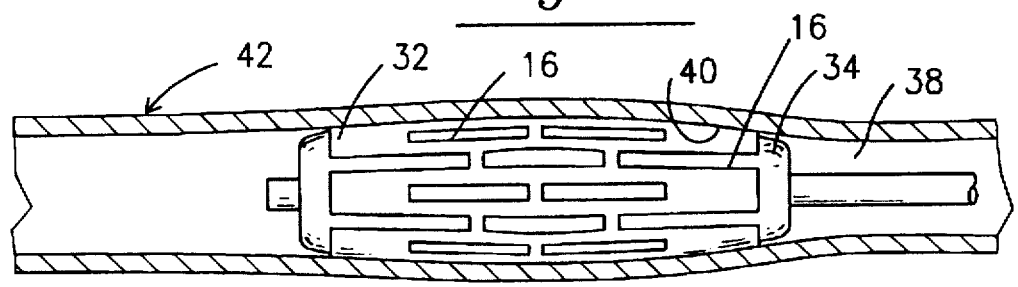
Fig. 5
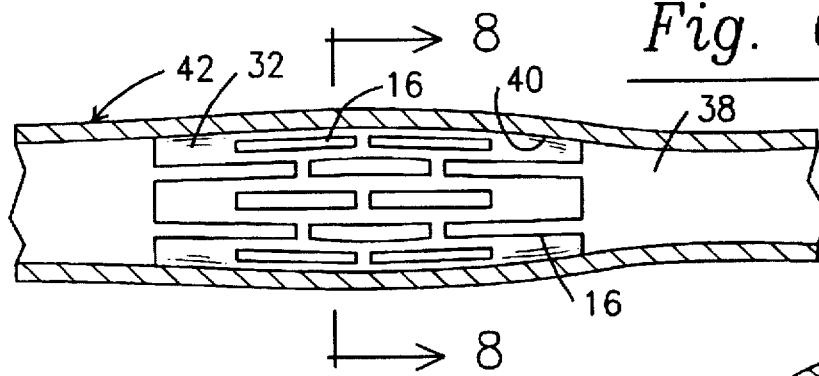
Fig. 6
Fig. 7
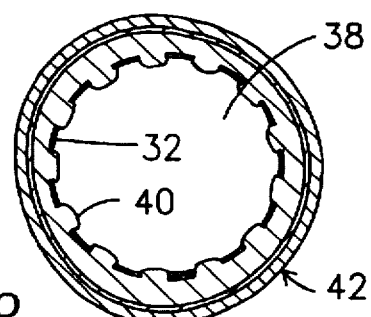
Fig. 8

SELF-LOCKING STENT AND METHOD FOR ITS PRODUCTION

This invention relates to expandable stents for use within body ducts. More particularly, it refers to an improved vascular stent mechanism used to repair damaged or blocked blood vessels.

BACKGROUND OF THE INVENTION

Various configurations for expandable grafts or stents are well known in the prior art. Examples are shown in U.S. Pat. Nos. 4,733,665; 4,739,762; 4,776,337; 5,102,417 and 5,195,984. While these grafts are useful for their intended purpose, there is a problem of migration that can occur which can have serious consequences to the patient. A tubular stent is needed that is self-locking in place within a blood vessel after removal of the delivery apparatus.

SUMMARY OF THE INVENTION

This invention solves the prior art problem of stents moving within a blood vessel by creating a self-locking stent for permanent positioning within a desired portion of a blood vessel. The stent is a tubular member with first and second ends and a plurality of longitudinally slots around the circumference of the tubular member. Rows of two or three slots are alternately spaced around the circumference of the tubular member. Each row is parallel to adjacent rows and the ends of the slots are spaced apart from adjacent slots. The tubular member is made from a flat sheet having opposed longitudinal edges with at least three holes along each edge. The holes along each opposed edge are aligned with corresponding holes on the other opposed edge and sutured together to form the tubular member. The tubular member is compressed over a balloon catheter and inserted into a desired portion of a blood vessel. The balloon at a tip of the catheter is expanded by application of pressure or volume of fluid or combination of both which presses the circumference of the tubular member into a vascular wall of the blood vessel to permanently lock the tubular member in place and cause minimal trauma to the inner wall of the blood vessel.

BRIEF DESCRIPTION OF THE DRAWINGS

The invention can be best understood by those having ordinary skill in the art by reference to the following detailed description when considered in conjunction with the accompanying drawings in which:

FIG. 4 is a side elevational view of the tubular member compressed over a balloon catheter;

FIG. 5 is a side elevational view of the tubular member and catheter of FIG. 4 positioned within a blood vessel shown in section;

FIG. 6 is a side elevational view of the tubular member and catheter expanded within a blood vessel shown in section;

FIG. 7 is a side elevational view of the tubular member locked in place within a blood vessel shown in section after the catheter is removed;

FIG. 8 is a cross-sectional view along line 8—8 in FIG. 7.

DETAILED DESCRIPTION OF THE INVENTION

Figure 1:
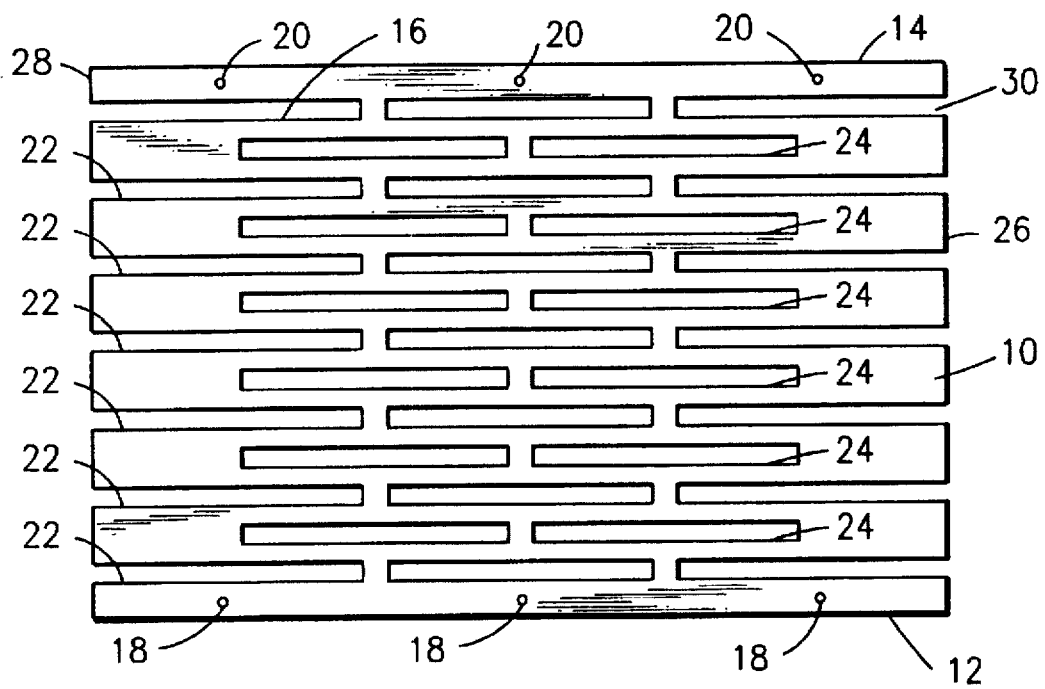
FIG. 1 is a top plan view of a flat longitudinal sheet used to form the tubular member of the invention.

Throughout the following detailed description, the same reference numerals refer to the same elements in all figures. Referring to FIG. 1, a flat sheet 10 having a general rectangular or square configuration and having longitudinal edges 12, and 14 is manufactured by using a laser cutting tool to prepare the slots 16 and holes 18 and 20 in either a sheet of metal or plastic. The metal can be stainless steel, titanium, nickel, a thermal alloy such as NITNOL or other metal compatible with a patient's vascular tissue. If metal is employed for the stent it can be coated with a biocompatible material such as polyurethane, polyethylene, silicone, block co-polymers of polyurethane, polyethylene and silicone, a biodegradable polymer such as polylactic acid, polyglycollic acid, and or hydroxy butyrate or valerate co-polymer. Biocompatible material will not interfere with blood or blood vessel interior wall tissue. The polymers can include anticoagulant agents, growth factor and like agents for reducing the reaction of blood to foreign surfaces.

Plastics employed to make the stent can be polyethylene, polyurethane, silicone or copolymer of polyurethane and polyethylene compatible with the vascular tissue of a patient.

The laser tool cuts out each of the slots 16 and holes 18 and 20 from a preprogrammed pattern. The configuration is important so that the holes 18 and 20 are located along edges 12 and 14, respectively of the sheet 10. Holes 18 are aligned and correspond to holes 20 on the opposed edge 14. Longitudinal slots 16 are cut out in a pattern whereby rows 22 have three longitudinal slots 16 and rows 24 have two longitudinal slots 16. More or less slots can be employed depending on the diameter of the artery. Side edges 26 and 28 of sheet 10 coincide with ends 30 of the longitudinal slots 16 in rows of three.

Figure 2:
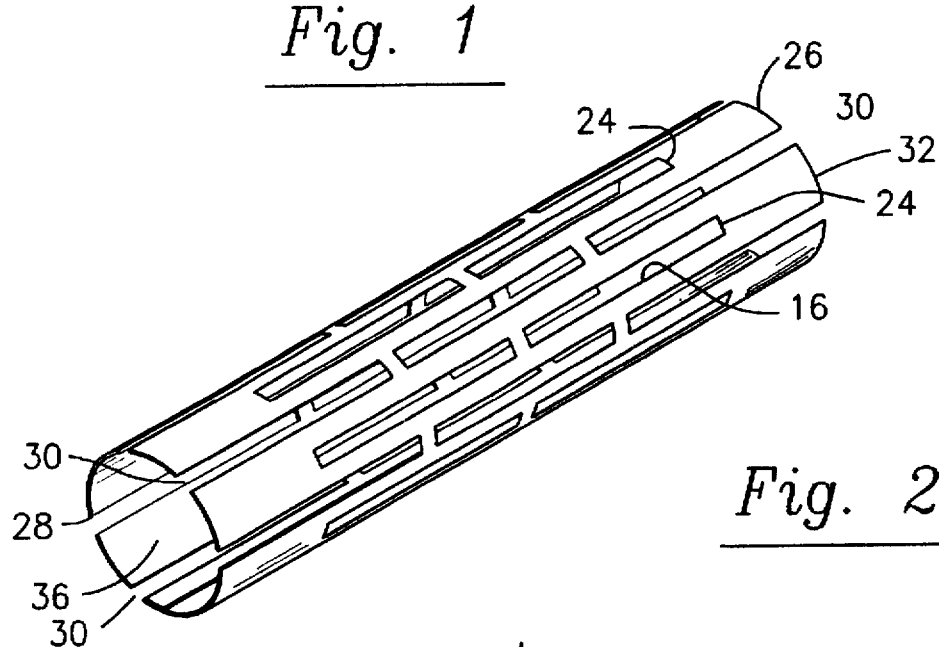
FIG. 2 is a perspective view of the flat sheet of FIG. 1 sutured together to form a tubular member.

In preparing the stent employed in this invention shown in FIG. 2, the flat sheet 10 is folded together so that each of holes 18 and 20 is aligned with the corresponding hole on the opposite side and then suture thread is run through the holes 18 and 20 to hold the stent 32 in a tubular configuration as shown in FIG. 2. The suture thread is made of biodegradable or non-degradable material and can be linked with a thin piece of metal.

Figure 3:
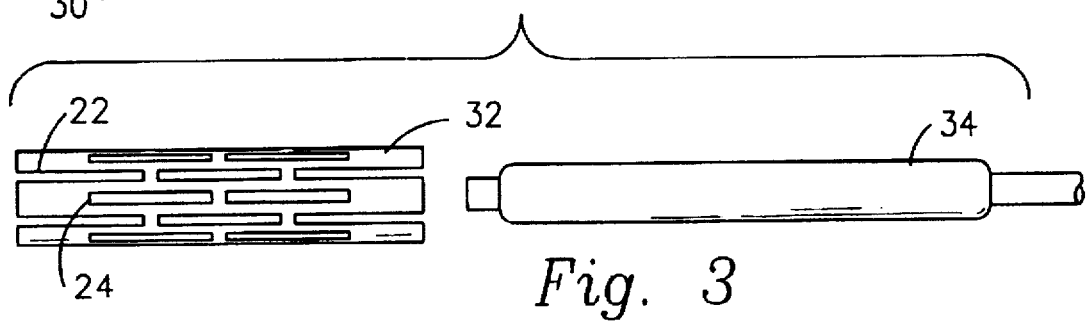
FIG. 3 is a side elevational view of the tubular member about to be compressed over a balloon catheter.

A balloon catheter 34 is inserted through opening 36 in the tubular member 32 as shown in FIGS. 3 and 4. The tubular member 32 is then passed with the balloon catheter 34 in place inside opening 36 into a vascular cavity 38 as shown in FIGS. 5–7. Catheter 34 is expanded as shown in FIG. 6 so that the tubular member 32 presses against the inner wall 40 of the blood vessel 42. The catheter 34 is then removed as shown in FIG. 7 and the tubular member 32 remains in place pressed against the inner side wall 40 of the vascular cavity 38. The position of the tubular member 32 within the vascular cavity 38 is shown in FIG. 8.

The configuration of tubular member 32 is such that the tubular member is locked in place in the side wall 40 of vascular cavity 38. The tubular member 32 thereafter cannot move and protects the side wall 40 from bursting.

If the length of stent deployed has to be more than a fixed length of 10 cms, then it is essential that two segments are placed close to each other and then a small knot is made at each edge 26 or 28 with the adjacent segment. The two segments, apart from providing the desired length, provide flexibility for the stent to negotiate tortious curves of the vascular system. If a fixed length of a long stent is used, it would not negotiate the curves. Numerous stents can be joined together like a train.

It is understood that the invention is not limited to the exact details of the construction operation and exact materials described herein. Equivalent materials can be substituted for the materials described herein.

Having thus described the invention what is claimed and desired to be secured by Letters Patent is:

1. An expandable vascular stent comprising:

a tubular shaped member having first and second ends and a wall surface disposed between the first and second ends, the wall surface having a plurality of parallel rows of longitudinal and spaced apart end to end slots, an alternating row of slots terminating at a portion of the tubular shaped member spaced from the first and second ends, the tubular shaped member having been formed from a flat rectangular sheet with opposed longitudinal edges, at least three, spaced apart suture holes along each opposed longitudinal edge, the holes from each longitudinal edge overlapping when the sheet is formed into the tubular shaped member and suture thread through each overlapping hole retaining the stent in its tubular shape, the tubular shaped member capable of being compressed over a balloon catheter and expanded within a desired portion of a blood vessel so that it is locked in place after the catheter is removed.

2. The expandable vascular stent according to claim 1 wherein the tubular shaped member is made from a metal compatible with vascular tissue.

3. The expandable vascular stent according to claim 1 wherein the tubular shaped member is made from a plastic compatible with vascular tissue.

4. The expandable vascular stent according to claim 1 wherein there are alternating rows of two and three longitudinal slots around a circumference of the wall surface.

5. The expandable vascular stent according to claim 4 wherein there are seven rows of three end to end spaced apart longitudinal slots each row of three slots separated by a row of two end to end spaced apart longitudinal slots.

6. The expandable vascular stent according to claim 1 wherein the suture thread is a thin piece of metal.

7. A method for manufacturing and implanting a stent within a blood vessel, the steps comprising cutting out multiple rows of longitudinal spaced apart slots in a flat rectangular sheet with opposed longitudinal edges and cutting out at least three holes along each longitudinal edge, forming the flat sheet into a tubular shaped member with the holes along each longitudinal edge aligned with a corresponding hole along the opposed longitudinal edge, tying suture thread to the aligned holes to retain the sheet in the tubular shape, compressing the tubular shaped member over a balloon catheter, inserting the catheter within a blood vessel by catheterization, providing expansion of the tubular shaped member at a desired location within the blood vessel by expanding a portion of the catheter over which the tubular shaped member is compressed to force the tubular shaped member radially outward into contact with a vascular wall of the blood vessel to lock the tubular shaped member in position within the blood vessel and then removing the catheter.

8. The method according to claim 7 having an additional step wherein two tubular shapes are tied together end to end prior to compressing the tubular shaped member over a balloon catheter.

9. The method according to claim 7 having an additional step wherein the tubular shaped member is coated with a biodegradable coating material compatible with blood and blood vessel interior cells.

10. The method according to claim 9 having an additional step wherein an anticoagulant or a growth factor for reducing the reaction of blood to a foreign surface is added to the biodegradable coating material.

11. The method according to claim 7 having an additional step wherein the tubular shaped member is coated with a non-degradable coating material compatible with blood and blood vessel interior cells.

12. The method according to claim 11 having an additional step wherein an anticoagulant or a growth factor for reducing the reaction of blood to a foreign surface is added to the nondegradable coating material.

13. The method according to claim 7 wherein the suture thread tied to the aligned holes is a thin piece of metal.

* * * * *